(12) United States Patent
Inao et al.

(10) Patent No.: US 7,317,197 B2
(45) Date of Patent: Jan. 8, 2008

(54) METHOD OF DETECTING TIGHTLY ADHERING STATE, TIGHT ADHESION CONTROL METHOD AND METHOD OF AND APPARATUS FOR NEAR FIELD EXPOSURE

(75) Inventors: Yasuhisa Inao, Kanagawa (JP); Toshihiro Fuse, Kanagawa (JP); Shinji Nakasato, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 728 days.

(21) Appl. No.: 10/834,862

(22) Filed: Apr. 30, 2004

(65) Prior Publication Data

US 2004/0223142 A1 Nov. 11, 2004

(30) Foreign Application Priority Data

May 8, 2003 (JP) .............................. 2003-129904

(51) Int. Cl.
*G01N 21/88* (2006.01)
(52) U.S. Cl. .................................. 250/548; 250/559.29
(58) Field of Classification Search ................ 250/548, 250/559.3, 559.29
See application file for complete search history.

(56) References Cited

U.S. PATENT DOCUMENTS

| 5,534,969 A | * | 7/1996 | Miyake ........................ 355/53 |
| 5,535,006 A | * | 7/1996 | Telschow et al. ........... 356/394 |
| 6,171,780 B1 | | 1/2001 | Pham et al. .................... 435/4 |
| 2004/0137338 A1 | | 7/2004 | Inao et al. ...................... 430/5 |
| 2004/0137339 A1 | * | 7/2004 | Inao et al. ...................... 430/5 |

FOREIGN PATENT DOCUMENTS

| JP | 62-139330 | 6/1987 |
| JP | 2000-19093 | 1/2000 |
| JP | 2002-231614 | 8/2002 |

* cited by examiner

*Primary Examiner*—John R. Lee
(74) *Attorney, Agent, or Firm*—Fitzpatrick, Cella, Harper & Scinto (57) ABSTRACT

A tightly adhering state between an elastically deformable first substrate deformed and made to tightly adhere to an elastically undeformable second substrate is detected by way of displacement of the light receiving position of a light receiving section adapted to receive light emitted from a light source for the first substrate and reflected by the first substrate.

9 Claims, 8 Drawing Sheets

LIGHT IRRADIATING SECTION

EXPOSURE MASK (THIN FILM SECTION)

FIG. 11

1004 REFLECTED-LIGHT-IRRADIATED AREA

1002

METHOD OF DETECTING TIGHTLY ADHERING STATE, TIGHT ADHESION CONTROL METHOD AND METHOD OF AND APPARATUS FOR NEAR FIELD EXPOSURE

BACKGROUND OF THE INVENTION

1. Field of the Invention

This invention relates to a method of detecting a tightly adhering state, a method of controlling tight adhesion using the detection method and a method of near filed exposure as well as to a device for detecting a tightly adhering state, a device for controlling tight adhesion using such a detection device and an apparatus for near field exposure.

2. Related Background Art

Semiconductor elements of electronic devices have been intensely required to be micronized in recent years to meet the demand for compact and low-profile electronic devices. For example, the design rules currently applicable to patterns of masks and reticles are intended to achieve line and space (L&S) of 130 nm on a mass production basis. This value is expected to be reduced further in the future.

Projection aligners (exposure apparatus), which have been in the mainstream in recent years, comprise an illumination optical system for illuminating a mask, utilizing a flux of light emitted from a light source and a projection optical system arranged between the mask and the object of exposure. In such a projection aligner, the limit for achievable resolution is generally believed to be substantially equal to the wavelength of the light source involved. It is difficult to form a pattern of 0.10 µm or less by means of a projection aligner if an excimer laser is used.

Additionally, if a light source for a shorter wavelength is found, light to be used for exposure with such a short wavelength cannot pass through the optical material used in the projection optical system (namely, the vitreous material of the lenses) so that consequently it cannot project light onto the object of projection and hence the latter cannot be exposed to light.

To cope with the problem, exposure apparatus realized by using the principle of scanning near filed microscopes (SNOMs) have been proposed in recent years as means for micro-processing with dimensions of 0.1 µm or less.

For example, U.S. Pat. No. 6,171,780 proposes an apparatus for exposing a local area of dimensions exceeding the wavelength of light of an object of exposure, which is resist, to near field light that seeps out of a micro-opening pattern of 100 nm or less formed on the surface of a mask that is elastically deformable along the normal line of the mask surface, while forcing the mask to tightly adhere to the resist.

However, if an exposure operation is conducted in such a near field exposure apparatus in a state where the elastically deformable mask does not tightly adhere to the object of exposure and separated from the latter to a region where near field light is not found, it is no longer possible to expose a local area of dimensions with more than the wavelength of light of an object to light. Therefore, a near field exposure apparatus adapted to expose an local area of an object of exposure to light in a state where a exposure mask is tightly adhering to the object requires to be provided with a means for ensuring that the exposure mask is tightly adhering to the object of exposure.

Techniques that can be used for observing a displacement of an exposure mask include one that is used for X-ray aligners and with which a laser beam is irradiated onto the exposure mask and observing the displacement of the reflected beam and one with which the displacement of an exposure mask is observed with an interferometer. However, since known exposure methods were devised for the purpose of exposing an object of exposure in a state where the object of exposure, which is photoresist, is separated from a photomask and therefore any technique for detecting if the photomask is tightly adhering to the object of exposure was not considered for them.

SUMMARY OF THE INVENTION

In view of the above identified circumstances, it is therefore the object of the present invention to provide a method adapted to accurately detect a tightly adhering state when an elastically deformable substrate is made to tightly adhere to an elastically undeformable substrate by deforming the former, a method of controlling tight adhesion using the detection method and a method of near filed exposure as well as to a device for detecting a tightly adhering state, a device for controlling tight adhesion using such a detection device and an apparatus for near field exposure.

According to the invention, there are provided a method of and a device for detecting a tightly adhering state, a method of and a device for controlling tight adhesion and a method of and an apparatus for near field exposure as will be described hereinafter.

In an aspect of the invention, there is provided a method of detecting a tightly adhering state between an elastically deformable first substrate deformed and made to tightly adhere to an elastically undeformable second substrate by way of displacement of the light receiving position of a light receiving section adapted to receive light emitted from a light source for said first substrate and reflected by said first substrate.

Preferably, with a method of detecting a tightly adhering state according to the invention, the tightly adhering state between said first substrate and said second substrate is detected on the basis of the light receiving position of said light receiving section receiving said reflected light as located substantially at the light receiving position of said light receiving section receiving said reflected light when said first substrate is in a perfectly undeformed state.

Preferably, with a method of detecting a tightly adhering state according to the invention, said light source for said first substrate includes a plurality of light sources and said light receiving section includes a plurality of light receiving sections adapted to receive light from said plurality of light sources.

Preferably, with a method of detecting a tightly adhering state according to the invention, said light receiving section comprises a plurality of optical detectors arranged at displaced positions for receiving said reflected light and the tightly adhering state is detected on the basis of detections of reflected light.

In another aspect of the invention, there is provided a tight adhesion control method that utilizes a method of detecting a tightly adhering state between a first substrate and a second substrate according to the invention.

In another aspect of the invention, there is provided a near field exposure method that utilizes a method of controlling tight adhesion between an exposure mask and photoresist.

In still another aspect of the invention, there is provided a device for detecting a tightly adhering state between an elastically deformable first substrate deformed and made to tightly adhere to an elastically undeformable second substrate, said device comprising: a light source for irradiating light onto said elastically deformable first substrate; a light receiving member for receiving light emitted from said light source for said first substrate and reflected by said first substrate and detecting the light receiving position of receiving the reflected light; and light receiving position determining means for determining, after a displacement of the light receiving position of receiving the reflected light as a result of elastic deformation of said first substrate as detected by said light receiving member, the return or non-return of the light receiving position substantially to the light receiving position of said light receiving section before said displacement.

In still another aspect of the invention, there is provided a tight adhesion control device that utilizes a device for detecting a tightly adhering state between a first substrate and a second substrate according to the invention.

In a further aspect of the invention, there is provided a near field exposure apparatus with controlling the tight adhesion of an exposure mask and photoresist that utilizes a tight adhesion control device according to the invention.

DESCRIPTION OF THE PREFERRED EMBODIMENTS

Now, the method of detecting a tightly adhering state according to the invention will be described by referring to the accompanying drawings that schematically illustrates an embodiment of the invention. In the illustrated instance, an exposure mask and an object of exposure are in a tightly adhering state.

Figure 1A:
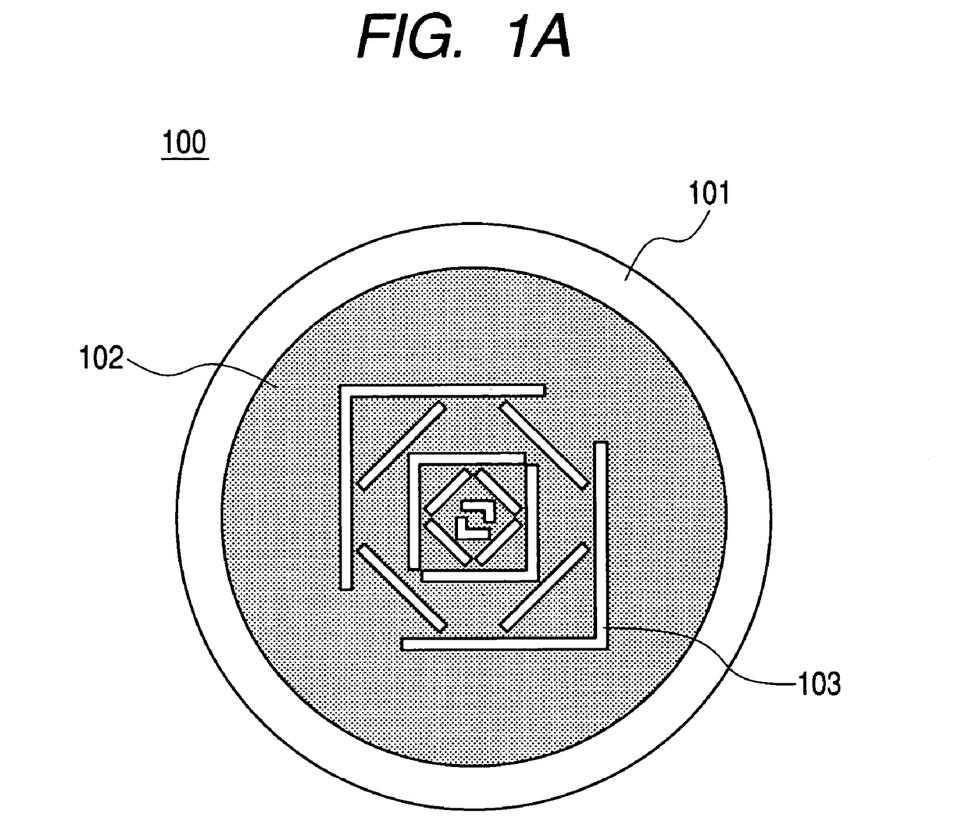
FIGS. 1A and 1B are schematic illustrations of the configuration of an exposure mask that is to be detected as object of detection in a tightly adhering state by means of an embodiment of device for detecting a tightly adhering state according to the invention.
Figure 1B:
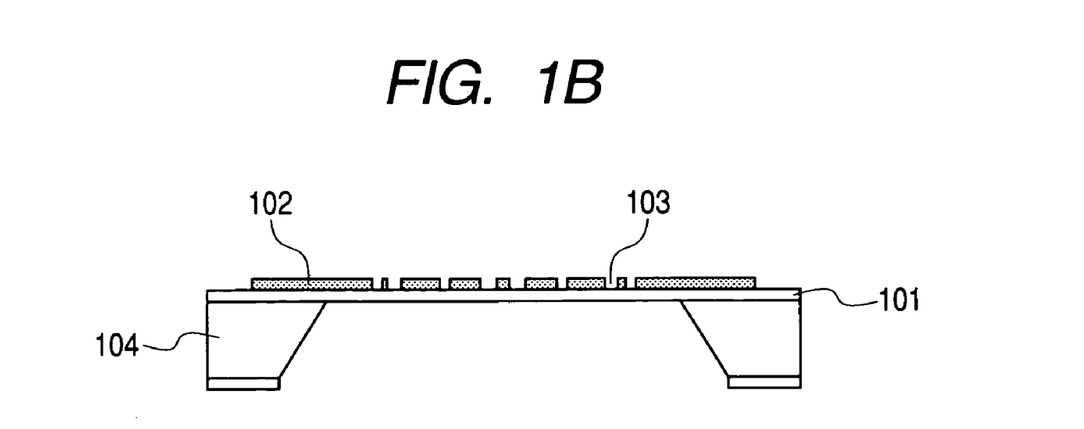
Figure 2:
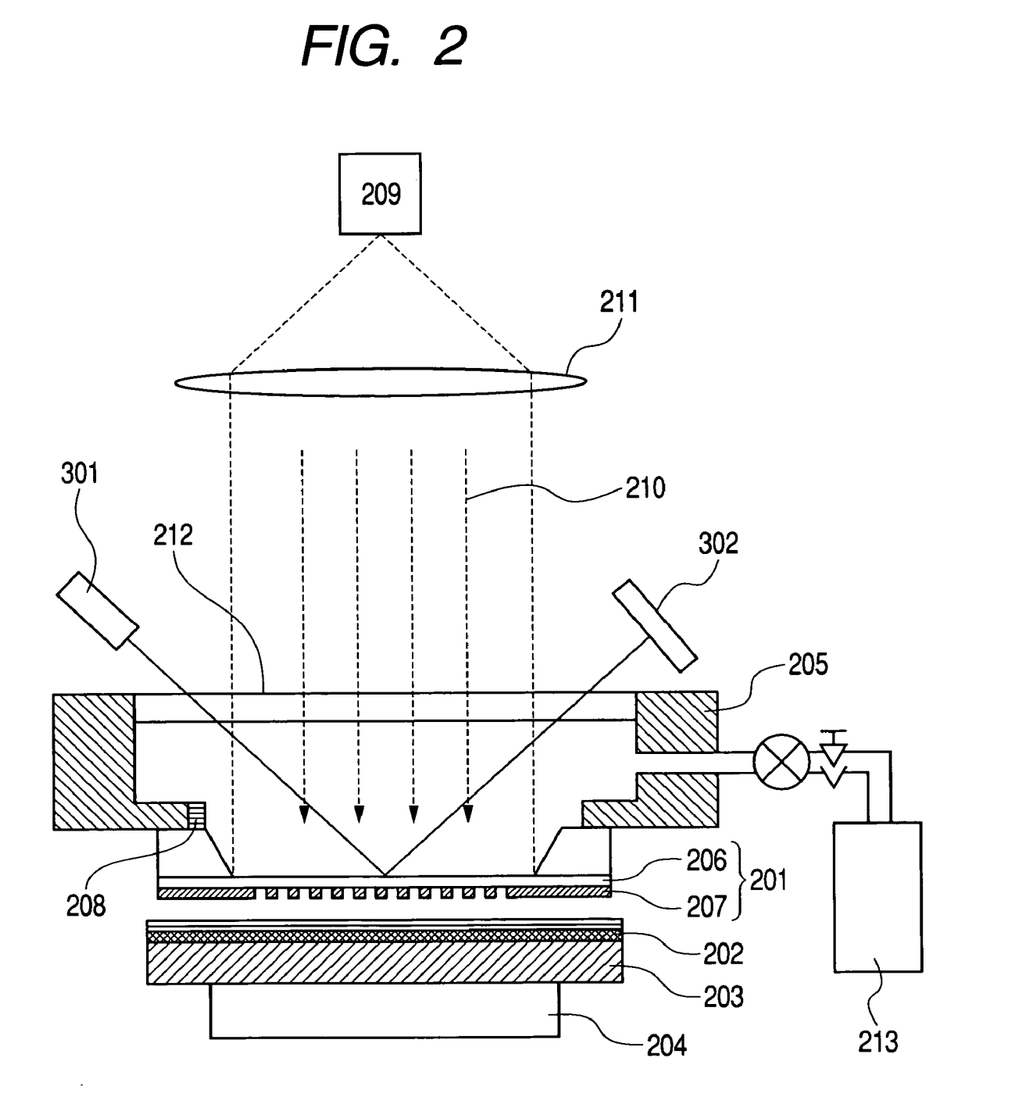
FIG. 2 is a schematic illustration of the configuration of an exposure apparatus to which an embodiment of device for detecting a tightly adhering state according to the invention is applied.

FIGS. 1A and 1B are schematic illustrations of the configuration of an exposure mask that is to be detected as object of detection in a tightly adhering state by means of an embodiment of device for detecting a tightly adhering state according to the invention. FIG. 2 is a schematic illustration of the configuration of an exposure apparatus to which an embodiment of device for detecting a tightly adhering state according to the invention is applied.

Firstly, the exposure mask 100 according to the invention will be described by referring to FIGS. 1A and 1B. FIG. 1A is a schematic view of the front surface side of the exposure mask that is used in the exposure apparatus of FIG. 2 and FIG. 1B is a schematic cross sectional view of the exposure mask. For the purpose of the invention, "front surface" refers to the surface where a light-shielding film is arranged and "rear surface" refers to the opposite surface.

The exposure mask 100 in FIGS. 1A and 1B is formed by using a mask support body 104, a mask base member 101 and a light shielding film 102. The light shielding film 102 is formed on the mask base member 101 and provided with micro-apertures 103, which show a desired pattern. The mask base-member 101 is made of an elastic material and realized in the form of a thin film.

Now, how the above described exposure mask is used in a near field exposure apparatus will be described by referring to FIG. 2.

Firstly, the exposure mask is placed in pressure adjustable container 205 of the near field exposure apparatus with its rear surface facing upward and the deflection of the exposure mask is adjusted by adjusting the pressure applied to it.

Resist 202 is formed on the surface of a substrate 203 as object of exposure. The resist 202/substrate 203 is arranged on stage 204 and the substrate 203 is aligned with the exposure mask 201 in terms of the intra-planar two-dimensions of the mask.

Then, the stage 204 is driven along the normal line of the mask surface to make the front surface of the exposure mask 201 tightly adhere to the surface of the resist 202 on the substrate 203 until the gap separating them is not greater than 100 nm over the entire surface.

Thereafter, exposure light 210 emitted from exposure light source 209 is collimated by a collimator lens 211 and transmitted through a glass window 212 before it is introduced into the pressure adjustable container 205 to irradiate the rear surface of the exposure mask 201 (from above in FIG. 2) in order to expose the resist 202 to light in a near field where light seeps out from the pattern of the micro-apertures cut through the light shielding film 207 on the mask base member 206 at the front surface of the exposure mask 201.

Now, the method of making the exposure mask to tightly adhere to the resist/substrate will be described in greater detail referring also to FIG. 2.

The exposure mask 201 and the resist 202 on the substrate 203 can be made to tightly adhere to each other over the entire surface of the latter if the front surface of the exposure mask 201 and the corresponding surface of the resist 202 are perfectly flat. However, in reality, the surface of the mask and that of the resist/substrate show undulations and therefore there may more often than not appear areas where they tightly adhere to each other and areas where they are not tightly adhering to each other if they are simply put together and brought to contact with each other.

However, the thin film section of the exposure mask 201 can be made to tightly adhere to the resist/substrate over the entire areas when the exposure mask 201 is elastically deformed so as to be bent and pressed against the resist 202/substrate 203 by applying pressure to the exposure mask 201 from the rear surface toward the front surface thereof.

As an exemplar technique for applying pressure onto the exposure mask 201, the exposure mask 201 is arranged so as to make its front surface face the outside of the pressure adjustable container 205 and its rear surface face the inside of the latter as shown in FIG. 2 and highly pressurized gas is introduced into the pressure adjustable container 205 by a pressure adjusting means 213 such as a pump until the internal pressure of the pressure adjustable container 205 becomes higher than the atmospheric pressure.

As highly pressurized gas is introduced into the pressure adjustable container 205 by the pressure adjusting means 213 to raise the internal pressure of the pressure adjustable container 205, the front surface of the exposure mask 201 and the surface of the resist 202 on the substrate 203 become to adhere to each other over the entire areas thereof under uniform pressure.

As pressure is applied by using the above described technique, the repulsive force acting between the front surface of the near field mask 201 and the surface of the resist 202 on the substrate 203 is made uniform due to the Pascal's principle. Therefore; the exposure mask 201 and the surface of the resist 202 on the substrate 203 will be not subjected to any locally strengthened force and neither the exposure mask 201 nor the resist 202/substrate 203 will be destroyed locally.

While the rear surface of the exposure mask is made to face upward in the pressure adjustable container 205 and pressure is applied from the rear surface side to the front surface side of the exposure mask 201 due to the pressure difference between the internal pressure of the pressure adjustable container 205 and the atmospheric pressure that is lower than the internal pressure for making the exposure mask 201 adhere to the resist 202/substrate 203 in the above described example, alternatively and inversely, the resist/substrate may be put on the front surface of the near field mask in a pressure reducible container so that pressure is applied from the rear surface side to the front surface side of the near field mask due to the pressure difference between the internal pressure of the pressure reducible container and the atmospheric pressure that is higher than the internal pressure. What is necessary is that the pressure applied to near field mask is higher at the rear surface side than at the front surface side thereof.

Now, an optical displacement sensor that is used in this embodiment will be described by referring to FIG. 2. The optical displacement sensor is applied to the near field exposure apparatus in order to detect the tightly adhering state of the exposure mask and the object of exposure.

More specifically, referring to FIG. 2, the optical displacement sensor comprises a light source 301 and a light receiving section 302. Light emitted from the light source 301 is irradiated onto the thin film section of the exposure mask 201 that is the object of detection. Light is emitted from the light source 301 in such a way that light reflected by the thin film section of the exposure mask 201 then strikes the light receiving section 302. As the exposure mask 201, which is the object of detection, is deformed, the position of the spot on the light receiving section 302 at which reflected light strikes it is shifted and the positional shift is read as the displacement of the exposure mask 201.

Now, the position of the spot on the light receiving section 302 at which reflected light strikes and which is shifted due to the deformation of the mask will be described in greater detail by referring to FIG. 4.

Figure 4:
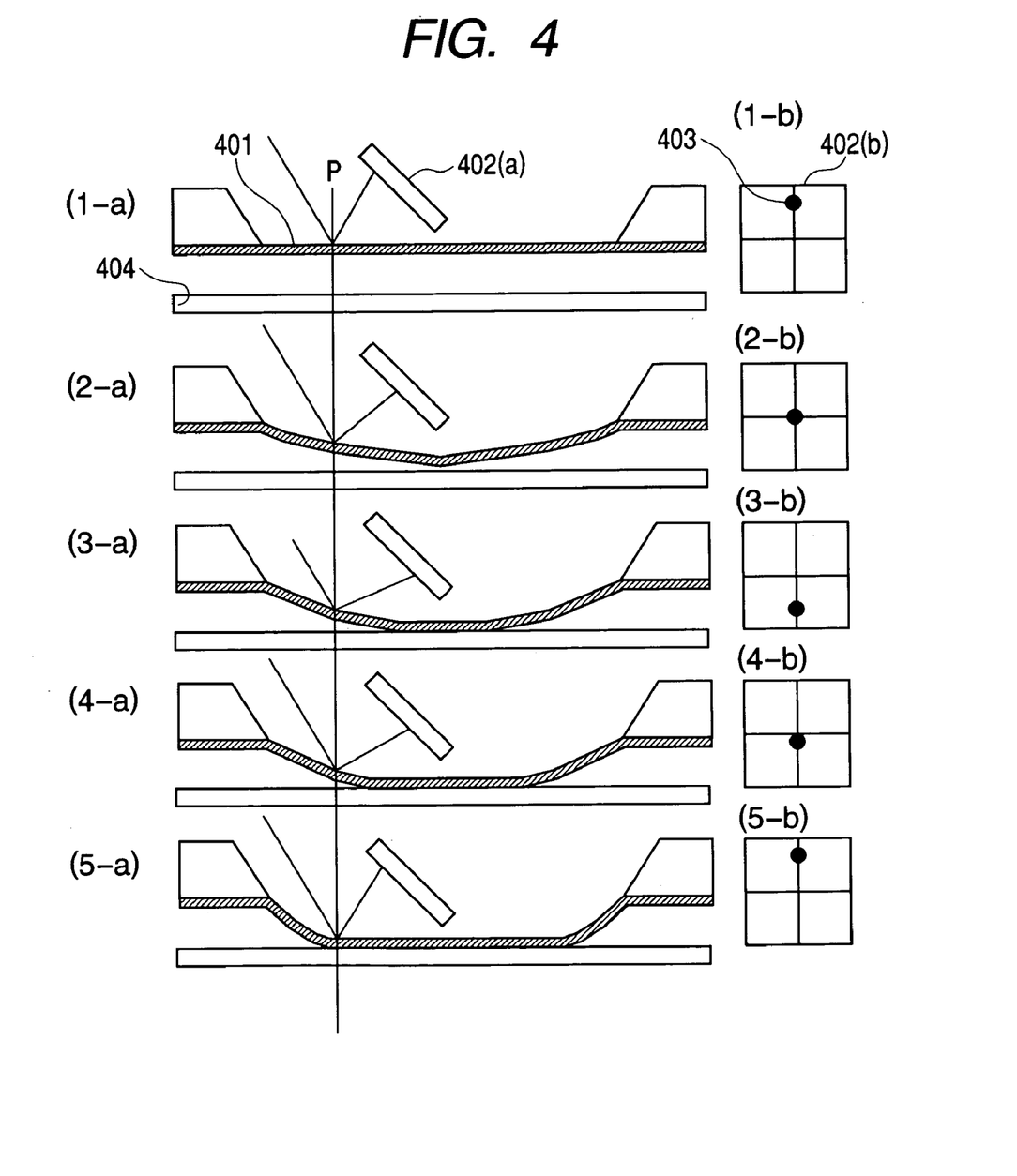
FIG. 4 is a schematic illustration of deformation of an exposure mask and positional shifts of a spot of reflected light on the light receiving section of the mask.

In FIG. 4, (*-a) indicates a change in the thin film and (*-b) indicates a positional shift of the spot 403 of reflected light that corresponds to (*-a) (* represents an integer between 1 and 5).

The squares in FIG. 4 show the light receiving section 402(b) when the light receiving section 402(a) is viewed from the light striking side thereof. The straight line denoted by P in FIG. 4 indicates the spot that is irradiated with light emitted from the light source.

Now, the process in which the exposure mask 401 comes to tightly adhere to the corresponding surface of the resist will be described in greater detail by referring to (1-a) through (5-a) in FIG. 4.

In FIG. 4, (1-a) indicates a state where the exposure mask is not bent at all. Assume here that the light source, the position of the spot of light irradiation P on the exposure mask and the position of the light receiving section 402 are so arranged that the spot 403 of reflected light on the light receiving section comes to position (1-b). As the exposure mask is bent thereafter, the spot of light irradiation P on the exposure mask is shifted to (2-a), to (3-a), to (4-a) and then to (5-a).

As shown in FIG. 4, the exposure mask is immediately before adhering to the object of exposure when the spot of light irradiation P is at (2-a). Then, the spot of light irradiation P is slightly inclined from its initial position on the exposure mask so that the spot of reflected light is shifted from (1-b) to (2-b) that is slightly lower than (1-b).

Thereafter, as the exposure mask starts tightly adhering to the object of exposure at the center thereof, the inclination of the exposure mask is increased so that the spot on the light receiving section of reflected light coming from the spot of light irradiation P is shifted downward. The inclination of the exposure mask is increased further and eventually it becomes largest at (3-a), when the spot of reflected light comes to (3-b), which is the lowest position.

As the exposure mask is bent further to increase the area of tight adhesion thereof, then inversely the inclination of the exposure mask at the spot of light irradiation P is reduced as shown at (4-a) and the spot of reflected light is shifted upward as shown at (4-b).

If the exposure mask is bent further, the exposure mask comes to tightly adhere to the object of exposure at the spot of light irradiation P as indicated by (5-a). In this state, the inclination of the exposure mask is same as that of the object of exposure and that of the exposure mask itself at the initial position so that the spot of reflected light is shifted upward substantially to the initial position as indicated by (5-b).

In this way, it is possible to detect that the exposure mask and the object of exposure tightly adhere to each other by seeing that a reciprocating cycle of the spot of reflected light 403 takes place on the light receiving section 402 between the time when the exposure mask starts being bent and the time when it tightly adheres to the object of exposure at the spot of light irradiation P and the spot of reflected light 403 returns to the initial position.

If the position of the spot of light irradiation P is selected to a position where the exposure mask does not tightly adhere to the object of exposure, the spot of reflected light does not come to the initial position. However, even in such a case, the exposure mask may tightly adhere to the object of exposure in the inside of the spot of light irradiation P. Then, if the relationship between the position of the spot of reflected light and the deflection of the exposure mask is known in advance, it is possible to know the extent to which the exposure mask and the object of exposure tightly adhere to each other from the position of the spot of reflected light even when the exposure mask does not tightly adhere to the object of exposure at the position of the spot of light irradiation P.

While the above described-arrangement requires calibration of the relation of the position of the spot of reflected light and the deflection of the exposure mask, it allows the extent to which the exposure mask and the object of exposure tightly adhere to each other at a position in the exposure mask that does not need to be exposed to light so that any influence of light coming from the light source 301 on the object of exposure can be completely eliminated.

After the operation of exposure to near field light, the exposure mask and the resist/substrate are peeled from each other in a manner as described below.

Firstly, the pressure in the pressure adjustable container 205 is reduced below the level of the atmospheric pressure by the pressure adjusting means 213 and the metal thin film on the exposure mask 201 is peeled off from the surface of the resist 202 on the substrate 203.

When the internal pressure of the pressure adjustable container 205 is reduced in a manner as described above in order to peel the exposure mask 201 off from the resist 202/substrate 203, the attractive force acting between the front surface of the exposure mask 201 and the surface of the resist 202 on the substrate 203 is made uniform due to the Pascal's principle. Therefore, the exposure mask 201 and the surface of the resist 202 on the substrate 203 will be not subjected to any locally strengthened force and neither the exposure mask 201 nor the resist 202/substrate 203 will be destroyed locally.

The attractive force acting between the exposure mask 201 and the resist 202/substrate 203, or the force pulling them to each other, can be controlled by adjusting the pressure in the pressure adjustable container 205. If, for example, the adhesion force between the surface of the exposure mask and that of the resist/substrate is strong, a relatively low pressure level is selected for the internal pressure of the pressure adjustable container 205 to increase the force pulling them away from each other. Then, the exposure mask and the resist/substrate can be peeled from each other relatively easily.

Now, the present invention will be described further by way of examples.

EXAMPLE 1

In this example, a sensor as described above was applied to a near filed exposure apparatus.

Figure 3:
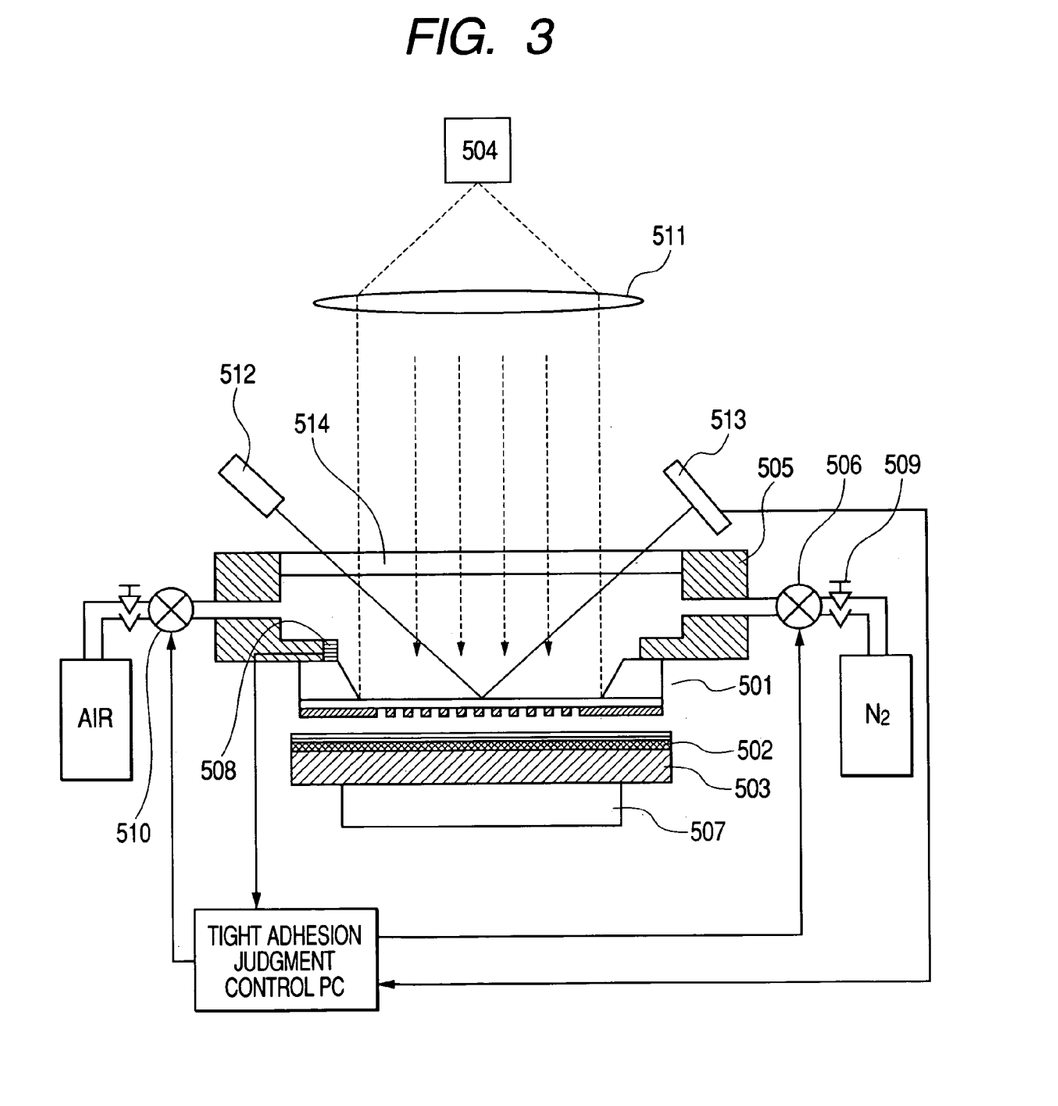
FIG. 3 is a schematic illustration of the configuration of the near field exposure apparatus provided with a sensor that is used in Example 1.

As shown in FIG. 3, photoresist 502, which was used as object of exposure, was applied to a substrate 503 and an exposure mask 501 was mounted on a hermetically sealed container 505 such that it was placed above the substrate 503 with its rear surface facing the inside of the container 505. The gap between the surface of the photoresist and the front surface of the exposure mask 501 was held to about 100 µm. The thin film part of the exposure mask 501 had dimensions of 10 mm×10 mm with a thickness of 1 µm. Then, the exposure mask 501 was bent to make it tightly adhere to the photoresist 502, while keeping the gap between the exposure mask 501 and the photoresist 502 unchanged. Then, nitrogen gas was allowed to flow into the hermetically sealed container 505 by opening a solenoid valve 506 in order to raise the internal pressure of the hermetically sealed container (pressure adjustable container) 505 relative to the external pressure.

At this time, the pressure sensor 508 arranged in the hermetically sealed container 505 was observed and the flow rate of nitrogen was adjusted by means of a flow rate regulator 509 so as to make nitrogen gas flow in at a pressurizing rate of 100 Pa/sec.

Figure 5:
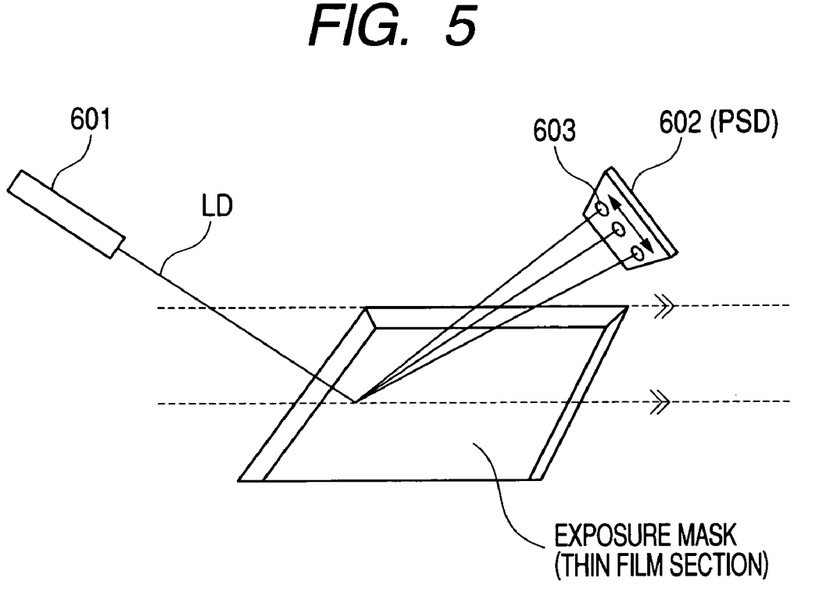
FIG. 5 is a view showing the relationship of the exposure mask, the light source and the light receiving section of Example 1.

Then, as shown in FIGS. 3 and 5, a laser beam LD having a wavelength of 630 nm and collimated to show a beam diameter of 100 µm was irradiated from a semiconductor laser 512 (601) arranged outside the hermetically sealed container onto-the exposure mask at a position separated from the center of the thin film section by 4 mm and the beam reflected from the exposure mask was received by a PSD (semiconductor position detector) 513 (602), which was a light receiving section arranged outside the hermetically sealed container. The laser beam was emitted in such a way that the optical axis of the laser beam was in parallel with the square frame of 10 mm×10 mm of the thin film as seen in FIG. 5.

As the internal pressure of the hermetically sealed container 505 changed at a rate of 100 Pa/sec, the thin film section of the exposure mask 501 was gradually bent. As a result of the deflection of the exposure mask 501, the position 603 of the spot on the PSD 602 receiving the reflected beam changed and the output voltage of the PSD changed accordingly.

Figure 6:
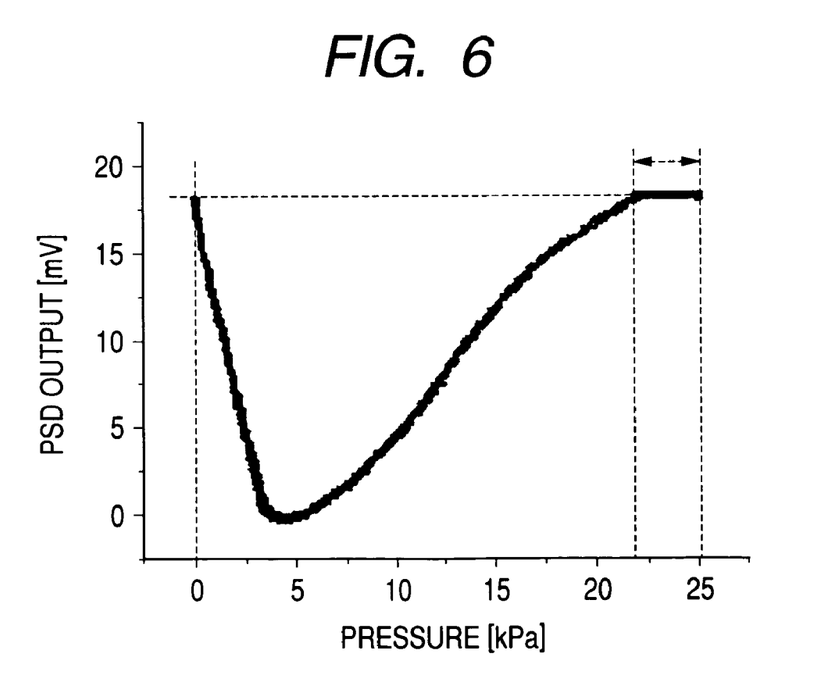
FIG. 6 is a graph showing the relationship of the pressure and the PSD in a tightly closed container.

FIG. 6 shows a graph showing the change in the output voltage of the PSD that was produced as a function of the change in the internal pressure of the hermetically sealed container 505. In FIG. 6, the vertical axis represents the output [mV] of the PSD. The spot of reflected light is located at an upper position of the light receiving section when the voltage value is high in FIG. 6. The horizontal axis in FIG. 6 represents the pressure in the hermetically sealed container 505.

As the inside of the hermetically sealed container 505 is pressurized, the output value of the PSD falls but rises once again beyond a certain pressure value to eventually get to an output level equal to the one for the pressure of 0 Pa. Once the output of the PSD gets to that level, it no longer changes (in the plateau zone indicated by the double-headed arrow in FIG. 6). The plateau indicates that the exposure mask and the photoresist tightly adhered to each other as described earlier by referring to an embodiment.

When it is found from the output of the pressure sensor 508 and that of the PSD 513 (602) that the output of the PSD no longer changes if the pressure is raised, the tight adhesion control PC determines that the exposure mask 501 and the photoresist 502 have tightly adhered to each other and closes the solenoid valve 506 and stops the inflow of nitrogen for raising the internal pressure.

Subsequently, g-line included in the output rays of a mercury lamp 504 (wavelength: 436 nm) are irradiated onto the photoresist for exposure. After the exposure, the solenoid valve 510 is opened to discharge the nitrogen in the inside of the hermetically sealed container 505 until the internal pressure of the hermetically sealed container 505 is reduced to the level of the atmospheric pressure and release the exposure mask 501 from deflection. The movement of the position of the spot of reflected light on the PSD when the exposure mask 501 is released from the deflection resembles to the one observed when the exposure mask 501 is made to tightly adhere to the photoresist, although the two movements are inverted relative to each other. More specifically, the output voltage value of the PSD falls to get to a bottom level when the internal pressure is reduced to a certain pressure level but rises back to regain the initial value as the internal pressure is reduced further. When the output voltage of the PSD regains the initial value, it is determined that the exposure mask is completely released from deflection.

Thereafter, the stage 507 is moved to another exposure region to repeat the exposure operation. Thus, the tightly adhering state of the exposure mask and the photoresist can be detected by monitoring the position of the spot of reflected light on the light receiving section and detecting the reciprocal movement of the position of the spot of reflected light.

EXAMPLE 2

In Example 2, the above-described embodiment was modified so as to detect a tightly adhering state by means of a plurality of photodiodes that were arranged at respective positions.

As in Example 1, a tight adhesion sensor was prepared and incorporated into an exposure apparatus in which an exposure mask was arranged with its rear surface facing the inside of a hermetically sealed container.

Figure 7:
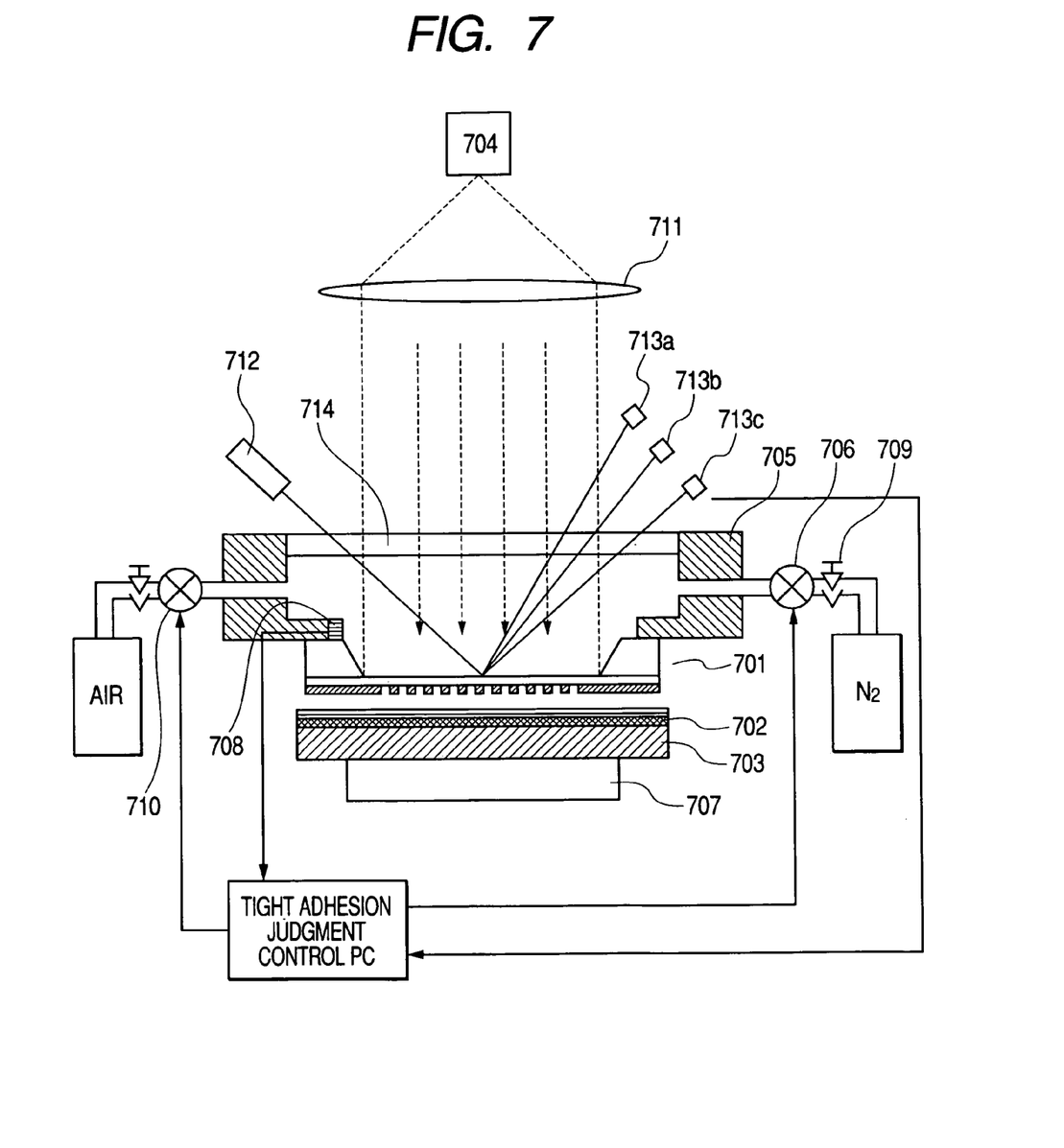
FIG. 7 is a schematic illustration of the exposure apparatus used in Example 2.

As shown in FIG. 7, photoresist 702, which was used as object of exposure, was applied to a substrate 703 and an exposure mask 701 was mounted on a hermetically sealed container 705 such that it was placed above the substrate with its rear surface facing the inside of the container. The gap between the surface of the photoresist and the front surface of the exposure mask was held to about 100 μm. The thin film part of the exposure mask had dimensions of 10 mm×10 mm.

Then, the exposure mask was bent to make it tightly adhere to the photoresist, while keeping the gap between the exposure mask and the photoresist unchanged. Thus, nitrogen gas was allowed to flow into the hermetically sealed container in order to raise the internal pressure of the hermetically sealed container relative to the external pressure. At this time, the pressure sensor arranged in the hermetically sealed container was observed and the flow rate of nitrogen was adjusted so as to make nitrogen gas flow in at a pressurizing rate of 100 Pa/sec.

Figure 8:
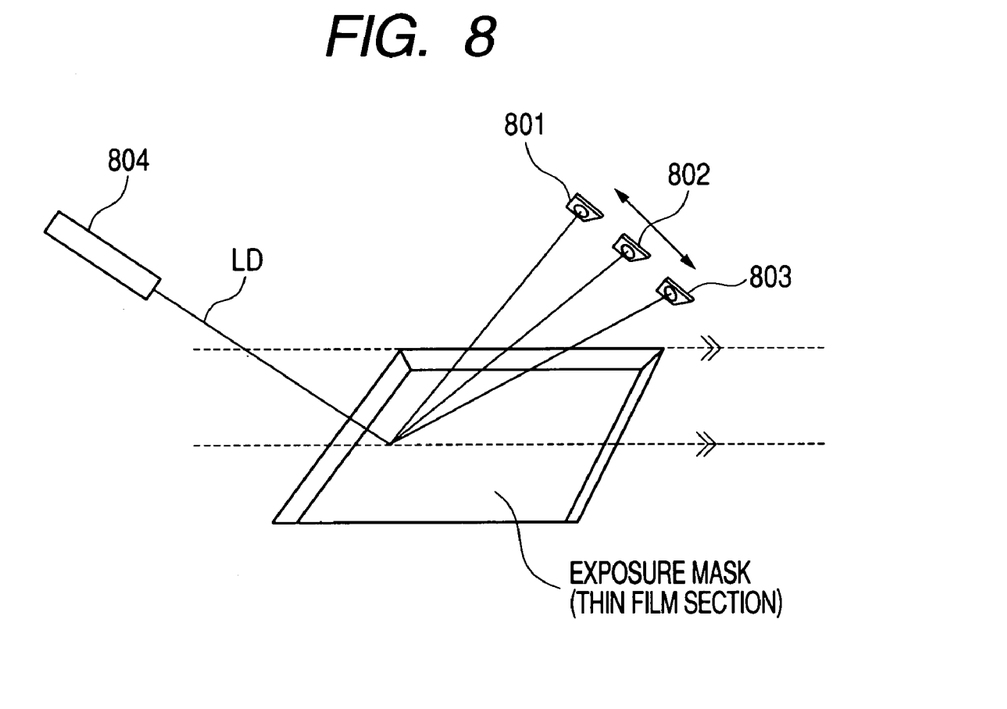
FIG. 8 is a schematic illustration of the relationship of the exposure mask, the light source and the light receiving section of Example 2.

Then, as shown in FIGS. 7 and 8, a laser beam LD having a wavelength of 630 nm and collimated to show a beam diameter of 100 μm was irradiated from a semiconductor laser 712 (804) arranged outside the hermetically sealed container onto the exposure mask at a position separated from the center of the thin film section by 4 mm and the beam reflected from the exposure mask was received by three photodiodes 713a through 713c (801a through 801c) arranged outside the hermetically sealed container. The laser beam was emitted in such a way that the optical axis of the laser beam was in parallel with the square frame of 10 mm×10 mm of the thin film.

When the exposure mask was not bent, reflected light formed a spot of light on the first photodiode 801. Then, as the internal pressure of the hermetically sealed container changed at a rate of 100 Pa/sec, the thin film section of the exposure mask was gradually bent. At this time, the position of the spot of reflected light passed through the second photodiode 802 and moved to the third photodiode 803.

As the exposure mask was bent further so as to tightly adhere more to the photoresist, the position of the spot of reflected light passed through the second photodiode 802 once again and returned to the first photodiode. Thus, the tight adhesion of the exposure mask and the photoresist, or the release of the exposure mask from deflection, can be detected when a reciprocating cycle of the spot of reflected light takes place and the spot of reflected light returns to the first photodiode 801. The first, second and third photodiodes were arranged on the straight line along which the spot of reflected light reciprocated. Thus, only the reciprocating motion of the position of the spot of reflected light was detected to detect the tight adhesion (or the release of the exposure mask from deflection.). In other words, the detecting operation was very simplified.

Thus, with the above described arrangement, it is possible to provide a sensor having a simple configuration for detecting a tightly adhering state of an exposure mask and resist at low cost.

EXAMPLE 3

In Example 3, the above described embodiment was modified so as to detect a tightly adhering state at a multiple of points.

As in Example 1, a tight adhesion sensor was prepared and incorporated into an exposure apparatus in which an exposure mask was arranged with its rear surface facing the inside of a hermetically sealed container.

Figure 9:
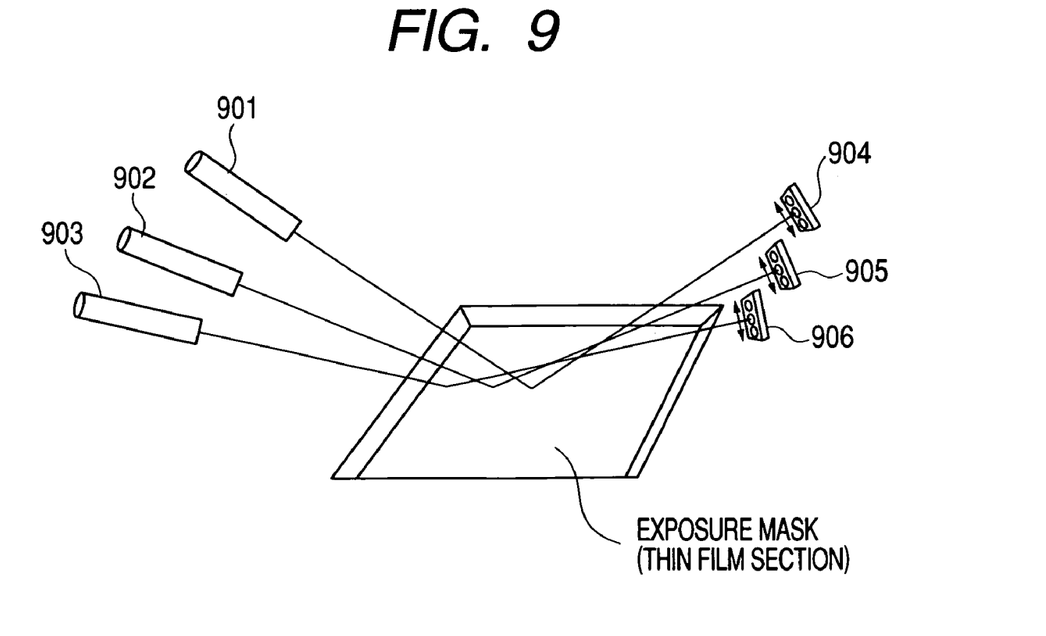
FIG. 9 is a schematic illustration of the relationship of the exposure mask, the light source and the light receiving section of Example 3.

In Example 1, a laser beam was irradiated from a semiconductor laser onto the thin film section of an exposure mask and the position of the spot of reflected light was detected to detect a tightly adhering state. However, since only a single laser beam was used for the detection, it was possible to detect only the tight adhesion (or the release of the exposure mask from deflection) of a single spot that was irradiated with a laser beam. In this example, three lasers 901, 902, 903 and three light receiving sections 904, 905, 906 were arranged in respective intra-planar directions of the plane in which the laser beam strikes the exposure mask as shown in FIG. 9 such that three laser beams were irradiated onto the thin film section of the exposure mask at three different positions to detect the tight adhesion (or the release of the exposure mask from deflection).

With this arrangement of detecting the tight adhesion (or the release of the exposure mask from deflection) at different positions, the region in which the exposure mask and the photoresist tightly adhere to each other can be detected in a stepwise fashion. In other words, the tight adhesion (or the release of the exposure mask from deflection) can be determined more accurately.

EXAMPLE 4

In Example 4, the above-described embodiment is modified so as to detect a tightly adhering state of an exposure mask two-dimensionally.

Figure 10:
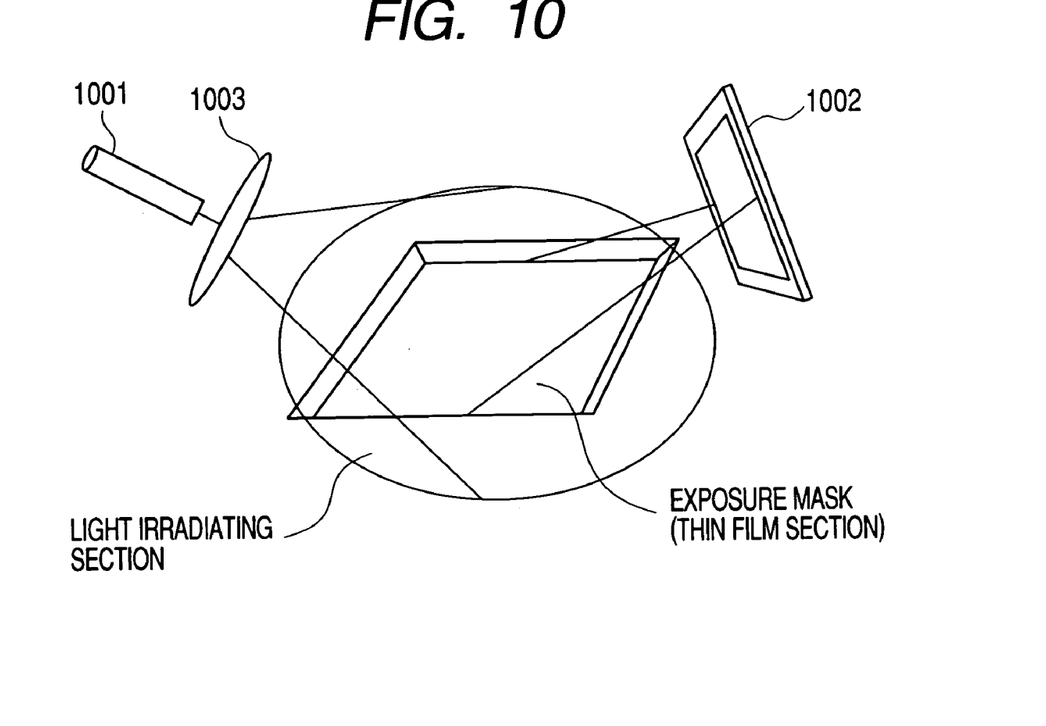
FIG. 10 is a schematic illustration of the relationship of the exposure mask, the light source and the light receiving section (CCD) of Example 4.

In Examples 1, 2 and 3, the tightly adhesion of the exposure mask was detected only at the position of the spot on the exposure mask where the laser beam was irradiated so that it was not possible to continuously detect the tightly adhering state in intra-planar directions of the exposure mask. In this example, the laser beam emitted from semiconductor laser 1001 is expanded by a beam expander 1003 as shown in FIG. 10 and irradiated as substantially collimated light so as to completely cover the exposure mask. A CCD 1002 is arranged in such a way that light reflected by the exposure mask can be detected by the CCD 1002 when the exposure mask is not bent.

Figure 11:
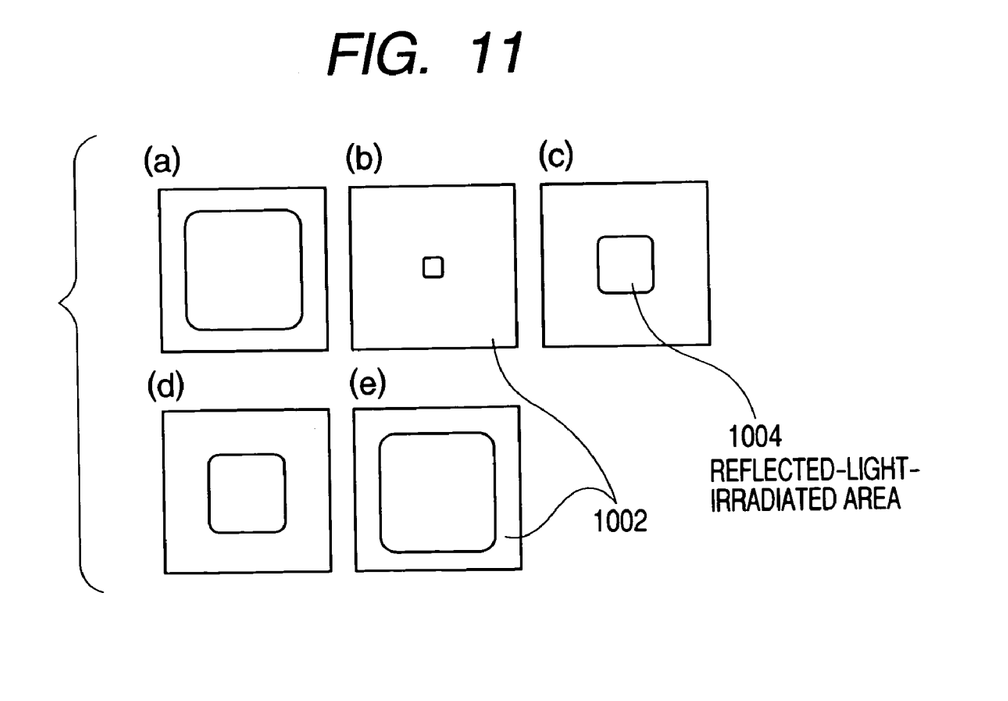
FIG. 11 is a schematic illustration of the areas on the light receiving section (CCD) of Example 4 irradiated by reflected light.

The profile of reflected light on the CCD changes in a manner as shown in (a) through (e) of FIG. 11 as the exposure mask was bent. In a state where the exposure mask was not bent, reflected light from the entire surface of the exposure mask is irradiated onto the CCD as shown in (a). As the exposure mask is bent, the area on the CCD that is irradiated by reflected light is reduced as shown in (b). As the exposure mask is bent further and made to tightly adhere to the substrate, the area 1004 irradiated by reflected light increases as a function of the area by which the exposure mask is made to tightly adhere to the substrate as shown in (c) through (e).

Thus, with the above described arrangement, the area on the CCD 1002 that is irradiated by reflected light changes as a function of the area by which the exposure mask is made to tightly adhere to the substrate so that the intra-planar area of the exposure mask that is made to tightly adhere to the substrate can be detected two-dimensionally. Therefore, the tightly adhering state can be detected continuously and the area by which the exposure mask tightly adheres to the substrate can be detected accurately.

Thus, according to the invention, it is possible to provide a method adapted to accurately detect a tightly adhering state when an elastically deformable substrate is made to tightly adhere to an elastically undeformable substrate by deforming the former, a method of controlling tight adhesion using the detection method and a method of near filed exposure as well as to a device for detecting a tightly adhering state, a device for controlling tight adhesion using such a detection device and an apparatus for near field exposure.

What is claimed is:

1. A method of detecting a tightly adhering state between an elastically deformable first substrate and an elastically undeformable second substrate, said first substrate being deformed and made to tightly adhere to said second substrate, said method comprising the steps of:
    emitting light from a light source onto said first substrate, such that the light is reflected by said first substrate and received by a light receiving member,
    measuring displacement of a position of the received light on said light receiving member, and
    detecting the tightly adhering state between said first substrate and said second substrate from the measured displacement of the position of the received light on said light receiving member.

2. A method according to claim 1, wherein the tightly adhering state is detected on the basis of the position of the received light as located substantially at a position where the light would be received if said first substrate were in a perfectly undeformed state.

3. A method according to claim 1, wherein said light source includes a plurality of light sources and said light receiving member includes a plurality of light receiving members adapted to receive light from said plurality of light sources.

4. A method according to claim 1, wherein said light receiving member comprises a plurality of optical detectors arranged at displaced positions for receiving the reflected light.

5. A tight adhesion control method of continuously applying force to an elastically deformable first substrate to deform it and make it tightly adhere to an elastically undeformable second substrate and terminating the application of force at the time of tight adhesion of said first substrate to said second substrate, said control method utilizing a method of detecting a tightly adhering state between the first substrate and the second substrate according any one of claims 1 through 4.

6. A near field exposure method for continuously applying force to an exposure mask to deform it and make it tightly adhere to a photoresist and terminating the application of force at the time of tight adhesion of the exposure mask to the photoresist, the method utilizing a tight adhesion control method according to claim 5.

7. A device for detecting a tightly adhering state between an elastically deformable first substrate deformed and made to tightly adhere to an elastically undeformable second substrate, said device comprising:
    a light source for irradiating light onto said first substrate;
    a light receiving member for receiving light emitted from said light source and reflected by said first substrate, and for detecting a position of the received light on said light receiving member; and
    a determining means for determining, after a displacement of the position of the received light on said light receiving member as a result of elastic deformation of said first substrate, the return or non-return of the position substantially to a position of the received light on said light receiving member before said displacement.

8. A tight adhesion control device comprising:
    means for continuously applying force to an elastically deformable first substrate to deform it and make it tightly adhere to an elastically undeformable second substrate; and
    adhesion control means for terminating the application of force to the first substrate at a time of detection by a device for detecting a tight adhesion of said first substrate to said second substrate;
    said control device including a device for detecting a tightly adhering state between a first substrate and a second substrate according to claim 7.

9. A near field exposure apparatus configured to continuously apply force to an exposure mask to deform it and make it tightly adhere to a photoresist and configured to terminate the application of force at the time of tight adhesion of said exposure mask by means of a tight adhesion control device to conduct near field light exposure, wherein said tight adhesion control device is constituted by a tight adhesion control device according claim 8.

* * * * *

UNITED STATES PATENT AND TRADEMARK OFFICE
CERTIFICATE OF CORRECTION

| | |
|---|---|
| PATENT NO. | : 7,317,197 B2 |
| APPLICATION NO. | : 10/834862 |
| DATED | : January 8, 2008 |
| INVENTOR(S) | : Inao et al. |

It is certified that error appears in the above-identified patent and that said Letters Patent is hereby corrected as shown below:

COLUMN 1:
        Line 59, "expose an" should read -- expose a --; and
        Line 60, "where a" should read -- where an --.

COLUMN 2:
        Line 12, "above identified" should read -- above-identified --.

COLUMN 3:
        Line 64, "illustrates" should read -- illustrate --.

COLUMN 4:
        Line 13, "cross sectional" should read -- cross-sectional --;
        Line 24, "above described" should read -- above-described --;
        Line 27, "in" should read -- in a --;
        Line 34, "two-dimen-" should read -- two dimen- --; and
        Line 55, "to-tightly" should read -- to tightly --.

COLUMN 5:
        Line 19, "above described" should read -- above-described --;
        Line 23, "Therefore;" should read -- Therefore, --;
        Line 35, "above" should read -- above- --; and
        Line 44, "near" should read -- the near --.

COLUMN 6:
        Line 45, "same" should read -- the same --.

COLUMN 7:
        Line 4, "above described-arrangement" should read -- above-described arrangement --;
        Line 48, "filed" should read -- field --; and
        Line 50, "object" should read -- an object --.

UNITED STATES PATENT AND TRADEMARK OFFICE
CERTIFICATE OF CORRECTION

PATENT NO. : 7,317,197 B2
APPLICATION NO. : 10/834862
DATED : January 8, 2008
INVENTOR(S) : Inao et al.

It is certified that error appears in the above-identified patent and that said Letters Patent is hereby corrected as shown below:

COLUMN 8:
Line 8, "onto-the" should read -- onto the --;
Line 55, "release" should be deleted; and
Line 56, "mask 501 from" should read -- mask 501 is released from --.

COLUMN 10:
Line 5, "above described" should read -- above-described --;
Line 12, "above described" should read -- above-described --; and
Line 47, "tightly" should read -- tight --.

COLUMN 11:
Line 4, "above described" should read -- above-described --.

COLUMN 12:
Line 7, "ing" should read -- ing to --; and
Line 50, "according" should read -- according to --.

Signed and Sealed this

Eleventh Day of November, 2008

JON W. DUDAS
*Director of the United States Patent and Trademark Office*